United States Patent [19]
Stevens

[11] 3,972,619
[45] Aug. 3, 1976

[54] METHOD AND APPARATUS FOR SURFACE ANALYSIS

[75] Inventor: Dennis Wakefield Stevens, San Diego, Calif.

[73] Assignee: General Atomic Company, San Diego, Calif.

[22] Filed: Aug. 11, 1975

[21] Appl. No.: 603,375

[52] U.S. Cl. ............................ 356/118; 350/15; 356/209
[51] Int. Cl.² ................................. G01N 21/40
[58] Field of Search .................. 356/118–119, 356/209, 33–35; 350/15, 159; 250/225

[56] References Cited
UNITED STATES PATENTS

| | | |
|---|---|---|
| 2,944,463 | 7/1960 | Rantsch .............................. 350/15 |
| 3,914,057 | 10/1975 | Smith et al. ........................ 356/118 |

*Primary Examiner*—John K. Corbin
*Assistant Examiner*—Wm. H. Punter
*Attorney, Agent, or Firm*—Fitch, Even, Tabin & Luedeka

[57] ABSTRACT

A method and apparatus are described for measuring anisotropy in the reflectivity within a region of a surface. The apparatus basically comprises a polarizing microscope which employs a rotating half-wave plate which rotates the polarization direction of the light incident upon the surface being examined and which also rotates the polarization direction of the light reflected from the surface being examined. The intensity of the reflected light passing through a polarizing filter is detected and related to the anisotropy.

11 Claims, 3 Drawing Figures

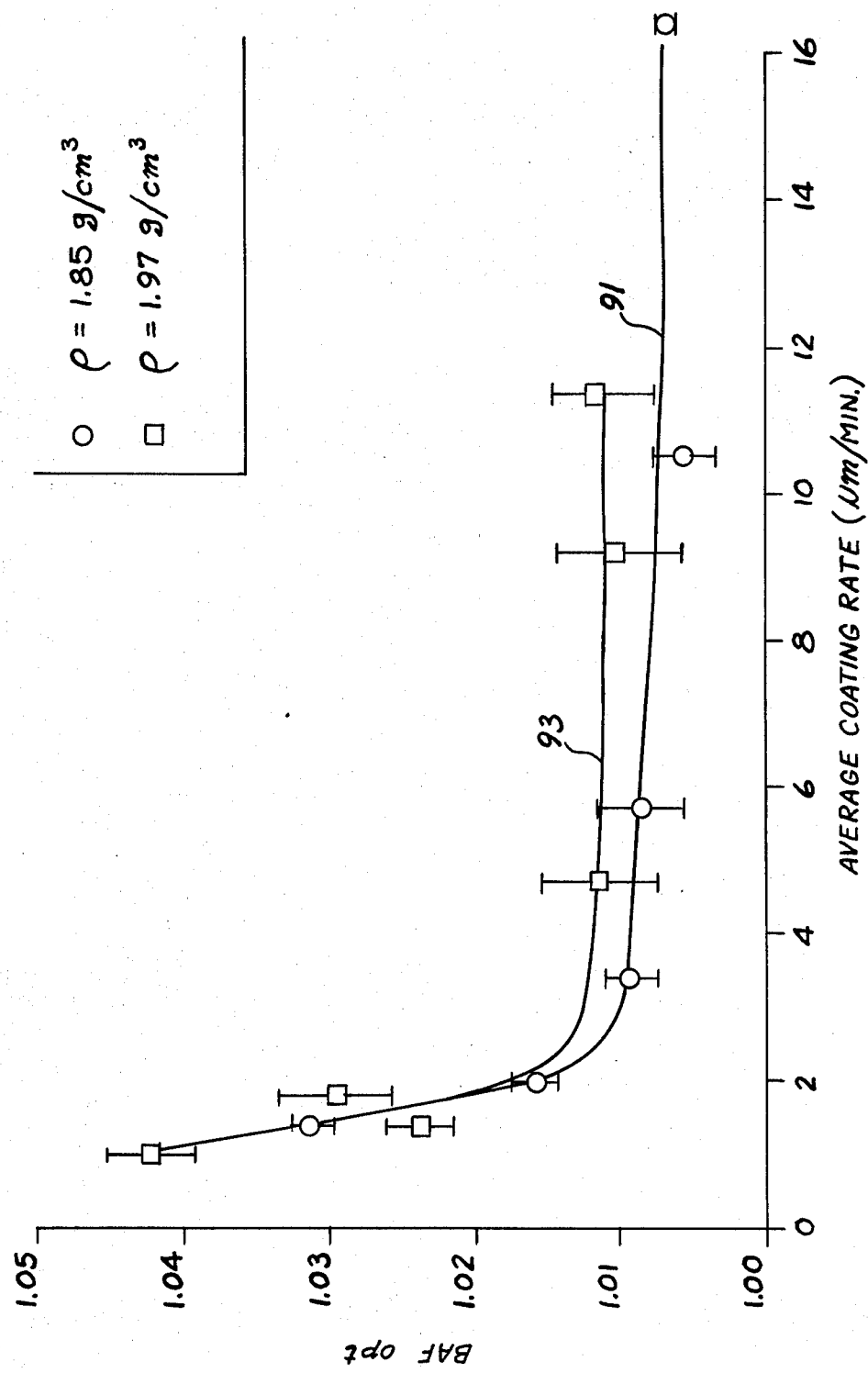

METHOD AND APPARATUS FOR SURFACE ANALYSIS

This invention relates generally to the measurement of optical anisotropy in the reflectivity of a surface for such purposes as determining the degree of crystalline orientation in the surface. More particularly, the invention relates to an improved method and apparatus for measuring anisotropy in the reflectivity within a region of a surface.

In the study of crystalline or pyrolytic materials of many kinds, it may be helpful to measure the optical anisotropy of a surface of the material. For example the dimensional stability of pyrolytic carbon coatings on nuclear reactor fuel particles may depend to a large extent on the crystalline orientation within the coatings. One way of determining the crystalline orientation is through the measurement of the optical anisotropy in the reflectivity of the coating. Other specific purposes for measuring optical anisotropy may arise in connection with research and development activities of various sorts.

A tool commonly in use for inspecting opaque materials is the polarizing microscope. A beam of monochromatic polarized light is directed at the surface being examined and the light reflected from the surface is focused to a magnified image of the region being examined by an objective lens. The reflected light passes through a polarizing filter and the intensity of the light passing through the filter is measured by using a photo-multiplier tube and associated electronic circuitry.

Several techniques are known in the prior art employing polarizing microscopes in order to measure optical anistoropy in an opaque surface. In one prior art technique, the specimen or surface being examined is rotated. The intensity of the light reflected from the surface is then measured as a function of the angle between the polarization direction of the incident light and the principal directions of the rotating surface. The ratio of the maximum to minimum reflectivity may then be empirically correlated to the degree of preferred crystalline orientation in the surface being examined. This technique suffers from a number of shortcomings including certain experimental errors inherent in the technique due to misalignment of the rotational axis of the specimen and other considerations.

Another technique somewhat similar to the above described maintains the surface being examined stationary and varies the polarization direction of the incident light by means of two polarizing filters. These filters are alternately inserted into the incident beam, and their transmission axes are mutually perpendicular. The reflected intensities corresponding to the two polarization directions are measured and after instrument corrections are made their ratio is determined. This ratio may then be related to the optical anisotropy of the surface. This technique suffers from certain deficiencies in that because it is only capable of measuring the reflectivities in two directions, these directions may not necessarily coincide with the principal directions of the surface being examined. Moreover, as the polarization direction of the incident light is varied, light losses in the instrument also vary and thus cause a variation in measured intensity which is independent of the properties of the specimen. As a result, a correction factor must be determined which introduces an additional source for experimental error.

An object of the present invention is to provide an improved method and apparatus for measuring anisotropy in the reflectivity within a region of a surface.

A further object of the invention is to provide an improved polarizing microscope for measuring optical anisotropy.

A more specific object of the invention is to provide an improved means for measuring optical anisotropy in the reflectivity of pyrolytic carbon coatings on nuclear fuel particles.

Still another object of the invention is to provide an improved method and apparatus for measuring optical anisotropy which is economical and practical for use for quality control, in research and development laboratories, or in other applications where routine measurements are made.

Other objects of the invention will become apparent to those skilled in the art from the following description, taken in connection with the accompanying drawings wherein:

FIG. 3 is a graph illustrating the type of information provided by the method and apparatus of the invention.

Very generally, in practicing the invention, a beam of monochromatic polarized light is directed at the region on the surface for which the optical anisotropy is to be measured. The reflected light beam from the surface is directed through a polarizing filter. The polarization directions of both the incident and reflected portions of the beam are rotated and the intensity of the light passing through the polarizing filter is detected. This intensity may then be related to the optical anisotropy of the region of the surface.

Figure 1:
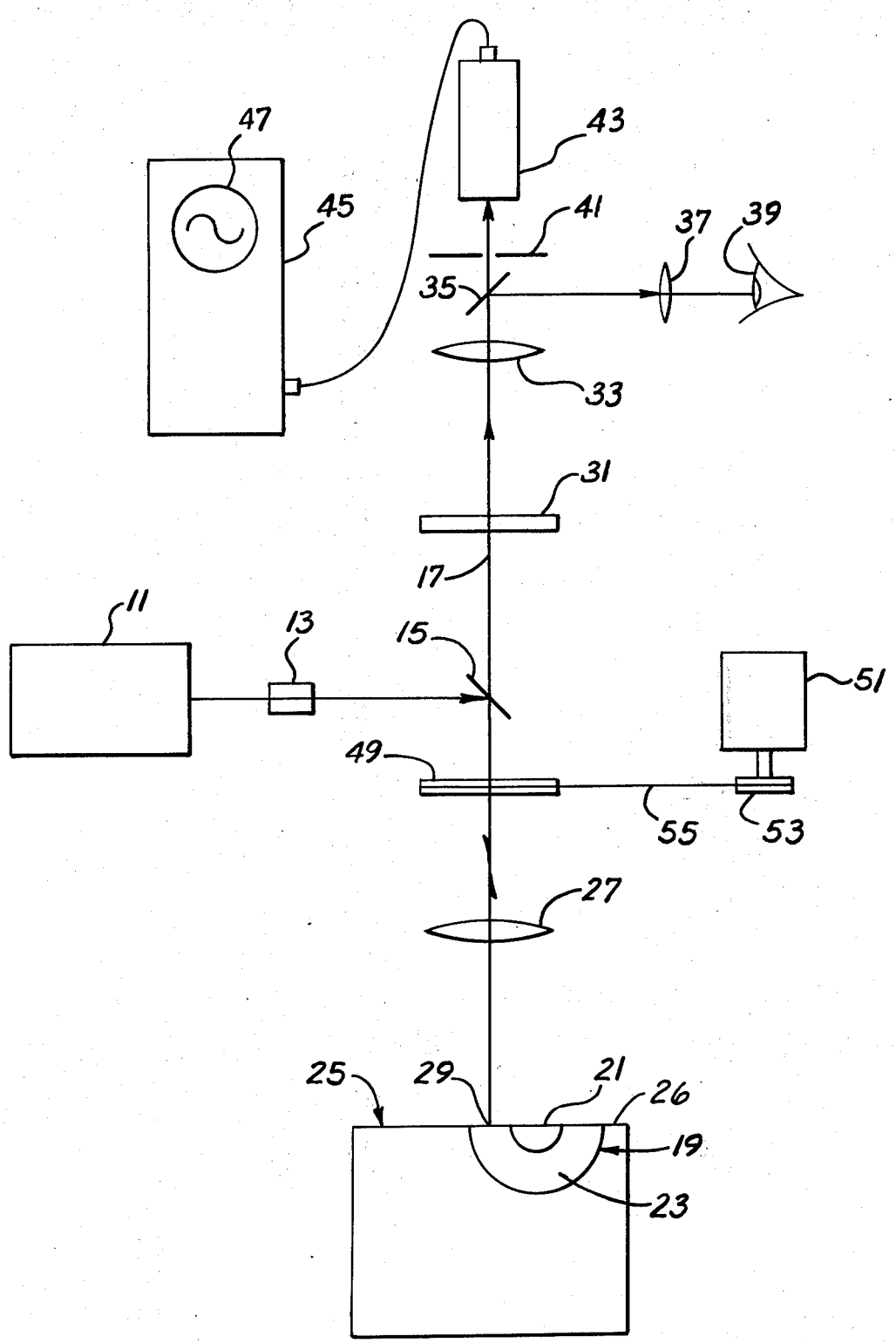
FIG. 1 is a schematic diagram of apparatus constructed in accordance with the invention.

The method of the invention will be best understood by first referring to a description of the structure and operation of the apparatus of the invention. A schematic diagram of the apparatus is illustrated in FIG. 1. Basically the apparatus illustrated in FIG. 1 is a polarizing microscope whose structure is modified to provide for rotation of the polarization directions of both the incident and reflected portions of the monochromatic polarized light beam. Other modifications, discussed below, are employed.

More particularly, the apparatus of FIG. 1 includes a source 11 of coherent monochromatic light such as a laser. The laser may be of any suitable type and may, for example, produce light at a wavelength of about 6,328 angstrom units. Light from the laser is directed through a suitable polarizing filter or prism 13 and is then reflected downwardly to the specimen by means of a semitransparent mirror 15 in a direction substantially coincident with the optical axis 17 of the apparatus.

The specimen being examined is indicated generally at 19 and comprises a nuclear fuel particle 21 provided with a coating 23 of pyrolytic carbon. The specimen 19 is supported in a specimen mount indicated generally at 25 and which will be described in greater detail below. Although described in connection with a pyrolytic carbon coated fuel particle, the invention is not limited thereto and is applicable to many fine-grained uniaxial materials.

In the case of a nuclear fuel particle as described, the fuel particle 19 is ground and polished down to the center of the spherical coated particle. If the grains in the coating 23 are oriented with cylindrical symmetry, then the grains will have a principal direction along the symmetry axis lying on the specimen surface being examined. A second principal direction will exist in the surface perpendicular to the first. The symmetry axis will tend to lie along the radial direction and the principal directions in the surface will then lie along the radial and tangential directions.

An objective lens 27 is utilized to focus the beam of coherent monochromatic polarized light at the particular region 29 lying on the specimen surface. After passing the objective lens 27, the reflected light is directed upwardly coincident with the optical axis 17 through a polarizing filter or analyzer 31. The light then passes through a condensing lens 33 to a beam splitter 35. Half of the light passes through an eyepiece lens 37 through which the specimen may be viewed by the naked eye as indicated at 39. The other half of the light passes through an aperture plate 41 to a photomultiplier 43. Electrical signals produced by the photomultiplier are passed to a suitable electronic system 45 including a cathode ray tube display 47.

In between the polarizing filter or analyzer 31 and the specimen 19, a half-wave plate 49 is mounted. The half-wave plate 49 is mounted to intercept both the incident beam between the mirror 15 and the objective 27, and the reflected beam between the objective 27 and the polarizing filter 31. The half-wave plate 49 may be a suitable micaretarder plate in a rotating housing, not shown. The plate is oriented in the housing with its plane generally perpendicular to the optical axis 17 and therefore perpendicular to the incident and reflected light beams. The axis of rotation of the plate 49 is preferably coincident with the optical axis 17 and thus both the incident and reflected light traverses through the plate in a direction perpendicular to the plane of the plate. A synchronous motor 51 is provided which drives a pulley 53 connected to the rotary plate 49 by a suitable belt 55. The motor is capable of rotating the half-wave plate 49 at a suitable and constant speed of, for example, about 300–400 rpm, which is about five or six cycles per second. Adequate anti-vibration components, not shown, are incorporated to minimize the vibration observable in the eye-piece 37. This is in order to prevent the image of the specimen from being significantly degraded.

Figure 2:
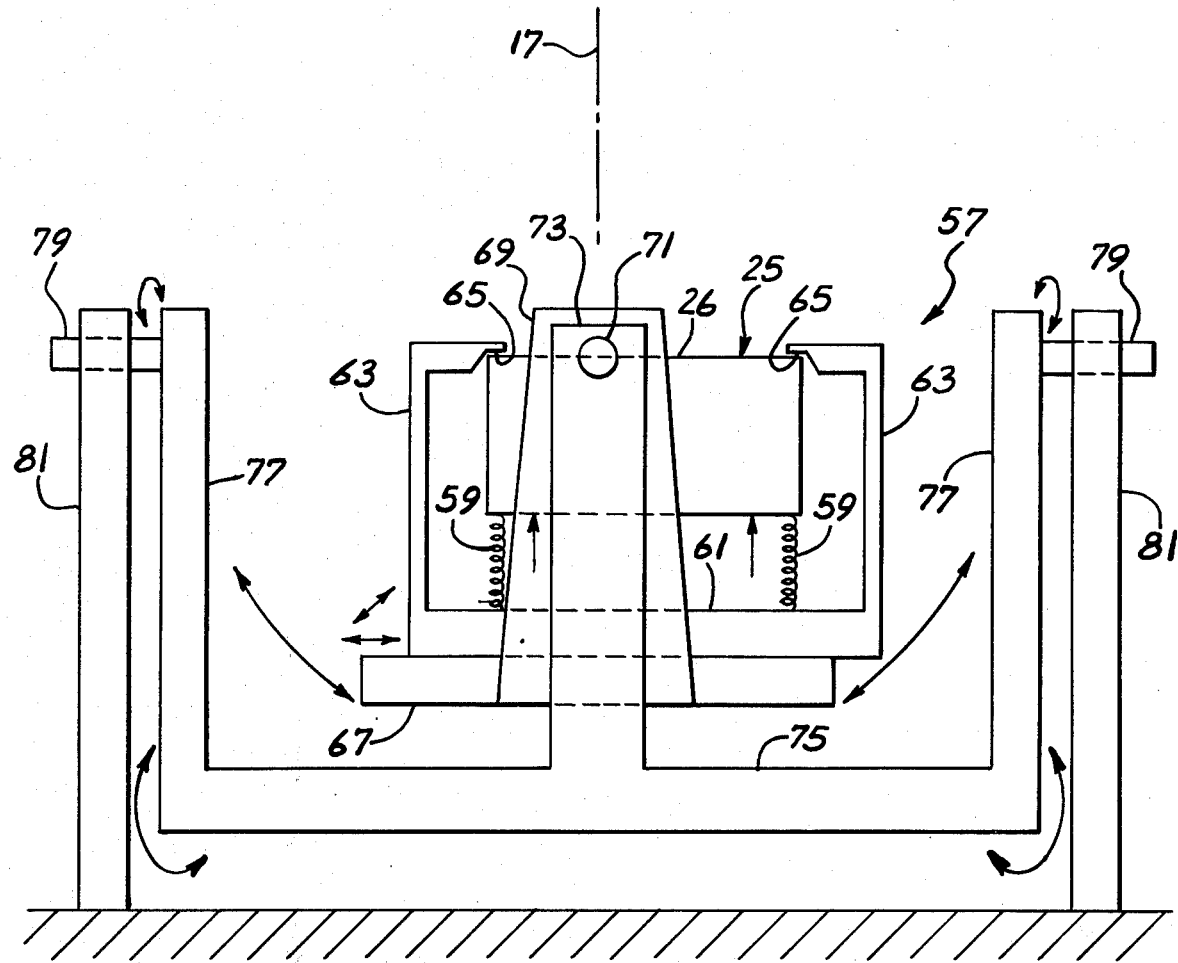
FIG. 2 is a schematic diagram of a specimen mount and universal stage which may be utilized in the apparatus of FIG. 1.

The specimen to be examined, in this example a carbon coated nuclear fuel particle, is molded into the upper surface 26 of the specimen mount 25. The upper surface is then ground down to the center of the spherical coated particle and highly polished so as to expose a cross section of the specimen in the plane of the upper surface 26. Specimen mount 25 may be supported by any suitable means. Preferably, however, the specimen mount 25 is supported in a universal stage 57 as illustrated in FIG. 2 which is so constructed as to allow simultaneous rotation of the normal to the reflecting surface at the region 29 about two mutually perpendicular axes both of which are also perpendicular to and intersect at the optical axis 17. The degree of tolerance between the actual point of intersection and the optical axis is preferably such that a 10° angular motion about the center of rotation in any direction does not cause the surface of the specimen 19 to go out of focus in the microscope.

Referring now more particularly to FIG. 2, the construction of a universal stage which may be used to support the specimen mount 25 is shown schematically. The specimen itself, not shown, is held in the specimen mount 25 with the surface being examined lying coincident with the top surface of the specimen mount 25. The specimen mount 25 may comprise any suitable metallographic holder.

The specimen mount 25 is supported on a plurality of coil springs 59 which are in turn supported on a stage 61. A plurality of retaining fingers 63 extend upwardly from the stage 61 and project inwardly to provide locating surfaces 65 against which the upper surface of the specimen mount 25 abuts. The stage 61 is mounted on a support plate 67 such that it is capable of movement with respect to support plate 67 with two mutually perpendicular rectilinear degrees of freedom. In the FIGURE, the stage 61 is shown displaced to the right with respect to the support plate 67.

The support plate 67 is provided with a pair of brackets 69 which extend upwardly on opposite sides thereof, and only one of which is visible in the drawing. The brackets 69 contain a pair of aligned pivot pins 71 which project outwardly therefrom and which are aligned on an axis which coincides with the plane of the top surface of the specimen mount 25. The axis of the pins 71 also intersects perpendicularly with the optical axis 17 of the apparatus. Locating surfaces 65 are machined with respect to the plate 67 and the position of the pins 71 to provide the desired locating relationship. Preferably, the distance between the upper surface of the specimen mount 25 (i.e. the reference plane of the locating surfaces 65) and the level of the axis of the pins 71 is less than 0.0005 inch (13 $\mu$m) to minimize apparent motion of the image of the specimen surface during rotation of the universal mount.

The pins 71 extend into the mounting brackets 73 for the outer part of the universal stage. The outer part of the universal stage includes two of the brackets 73, only one of which is visible, which extend upwardly from a base 75. The base 75 is provided with two upwardly extending brackets 77 which contain a pair of outwardly extending axially aligned pivot pins 79. The pins 79 extend into mounting posts 81 and are aligned on an axis which lies substantially in the plane of the top surface of the specimen mount 25 with the same tolerance as that of the axis of pins 71, and which intersects the axis of the pins 71 normal thereto and normal to the optical axis 17. The resultant universal joint enables displacement of the specimen surface being examined without deterioration in the focus of the microscope. Adjustment and angular position of the universal joint may be made by suitable micrometer screws, not shown, sufficient to cause plus or minus 10° of rotation (20° total) about the center of rotation of the universal joint. The XY stage 61, together with adjustment of the universal joint, enables sufficient freedom in the placement of the surface of the specimen being examined so that the specimen reflecting surface may be moved through the field of view of the microscope without altering the alignment of the optical axis of the microscope with the center of rotation of the universal joint.

The method will now be described as used in connection with pyrolytic carbon coated fuel particles for high temperature gas cooled nuclear reactors. It will be apparent, however, that the method is applicable to many fine-grained uniaxial materials. The specimen is first placed in the specimen mount 25, which may be of standard 1¼ inch (3.18 centimeter) diameter metallographic mount. The specimen is oriented in the specimen mount so that the mutually perpendicular principal directions will lie in the specimen surface.

When the polarized light is directed at the surface of the specimen, local micron size regions on the surface (referred to as optical domains or just domains) cause the light to become slightly depolarized. This is because these domains will have principal directions which are misoriented with respect to those of adjacent domains. The analyzer or polarizing filter 31 is rotated about an axis perpendicular to its plane to a position where the light sensed by the photo-multiplier 43 is minimized. In this position, the polarized portion of the reflected light beam is completely absorbed by the polarizing filter 31, and one-half of the depolarized intensity is observed and measured. This minimum intensity is then recorded as $I_0$ (in arbitrary units). The analyzer or polarizing filter 31 is then rotated or displaced by a small angle $\epsilon$ (for example about 5°) from the minimum intensity position. The reason for this will be understood from the explanation below.

The polarization direction of the incident light is caused to rotate continuously by means of the rotating half-wave plate. The polarization direction of the reflected light is also rotated by the half-wave plate in an amount equal in magnitude but opposite in the direction as compared to the rotation of the polarization direction of the incident light. The net rotation of the polarization direction results only from reflection from the sample as a result of the optical anisotropy of the specimen and the polarization direction of the incident light with respect to the principal directions of the specimen surface (i.e. of the aggregate of domains). As the polarization direction of the incident light is rotated by the halfwave plate 49, the displacement of the polarization direction of the reflected light from that of the incident light oscillates. The amplitude of this oscillation may be determined by measuring the amplitude of the oscillations in intensity of the light passing the polarizing filter 31 and being detected by the photomultiplier 43. The limits of these oscillations are defined $I_1$ and $I_2$ (again in arbitrary units). By adjusting the universal mount 25, these oscillations may be made constant from cycle to cycle. It is then possible to determine the magnitude of the amplitude of oscillations in the displacement of the polarization direction of the reflected light from that of the incident light (an amplitude defined as $\beta$). The parameter is determined as set out below and is defined as the rotary power of the sample.

$$\sin \beta = \frac{1}{2} \frac{I_2 - I_1}{I_2 + I_1 - 2I_0} \sin \epsilon .$$

The ratio of the minimum intensity $I_0$ to the maximum intensity obtained by displacing the analyzer or polarizing filter 31 90° from the position of the corresponding minimum intensity may also be obtained by these measurements. This parameter, designated as $\alpha$ is found as follows:

$$\alpha = \frac{2I_0}{I_2 + I_1 - 2I_0} \sin^2 \epsilon .$$

The degree of polatization (i.e. the polarized fraction) may then be determined as follows:

$$P = \frac{1-\alpha}{1+\alpha}.$$

The depolarized fraction is therefore:

$$1 - P = \frac{2\alpha}{1+\alpha}.$$

Measurements of the depolarized fraction can be analytically related to the optical anisotropy within individual domains which in turn can be empirically related to preferred crystallite orientation within individual domains.

A preferred orientation parameter $O_p$, which may range from zero to unity, with unity being total alignment of the domains or grains and with zero being complete randomness, may be obtained as follows:

$$O_p = \frac{\beta}{\sqrt{2\alpha + \beta^2}}$$

Thus, it may be seen that the parameters $\alpha$ and $\beta$ may be analytically related to the degree of alignment of domains with respect to one another. The two preferred orientation parameters (the preferred orientation of crystallites within individual domains and the degree of alignment of the domains with respect to one another) can then be combined and related to the degree of preferred orientation of crystallites in the aggregate of domains. Thus, the two parameters $\alpha$ and $\beta$ yield a total of three preferred orientation parameters. However, they are related to one another so that any two of the parameters can be considered to be independent (i.e. any one preferred orientation parameter can be uniquely determined from the other two).

The method and apparatus of the invention provide parameters $\alpha$ and $\beta$ which may be used to fully characterize optical anisotropy and hence preferred orientation in pyrolytic carbons and similar uniaxial materials. Artifactitious variations in measured intensity are minimized because the same regions on the mount surface are studied during rotation of the polarized light beam. Alignment problems are virtually non-existent compared with prior art apparatus. Moreover, the normal to the sample surface may easily be aligned parallel to the optical axis of the microscope. The fact that the principal directions of the surface being analyzed do not lie along the radial and tangential directions is readily accommodated because the polarization direction is scanned in all directions on the specimen surface. Light losses and a consequent need for an instrument correction factor are avoided.

Referring to FIG. 3, measurements on a test region of a specimen using the method and apparatus of the invention are illustrated. The results are expressed as optical determination of the Bacon Anisotropy Factor plotted against the average coating rate at which the carbon coating was deposited. The curve designated as 91 represents a density of 1.85 grams per cubic centimeter whereas the curve designated 93 represents a density of 1.97 grams per cubic centimeter. It may be seen that data obtained in accordance with the invention varies systematically with coating rate, initially falling sharply with increasing coating rate and then falling slowly above a coating rate of 3 μm per minute. In addition, some influence of density is indicated at high coating rates. Data obtained from prior art techniques typically exhibits considerable scatter as a consequence of random experimental error, making it difficult to resolve the difference between samples prepared at different coating rates.

It may therefore be seen that the invention provides an improved method and apparatus for measuring optical anisotropy. By direct measurement of rotary power, experimental error is significantly reduced from prior art methods and apparatus. The ability to measure the depolarization parameter enables complete characterization of optical anisotropy. The apparatus is relatively simple of construction and thereby experimental error is minimized. The provision of a universal mount provides a convenient means for aligning the specimen with the microscope without the specimen surface moving in the field of view or going out of focus in the microscope.

Various modifications of the invention will become apparent to those skilled in the art from the foregoing description and accompanying drawings. Such modifications are intended to fall within the scope of the appended claims.

What is claimed is:

1. A method for measuring anisotropy in the reflectivity within a region of a surface, comprising, directing a beam of monochromatic polarized light at the region on the surface, directing the reflected light beam through a polarizing filter analyzer, rotating the polarization directions of both the incident and reflected portions of the beam, and detecting the intensity of the light passing through the analyzer.

2. A method according to claim 1 wherein the analyzer is oriented such that the light passing through the analyzer provides information on the intensity of the oscillations of the angular displacement between the polarization direction of the incident beam and the polarization direction of the reflected beam.

3. A method according to claim 1 wherein the analyzer is first rotated to a position wherein the light passing through the analyzer when the polarization directions of the incident and reflected portions of the beam are not rotated in minimum, wherein the analyzer is then displaced by an angle ε from the position of minimum intensity, wherein the polarization directions of both the incident and reflected portions of the beam are rotated, wherein the surface of the specimen is adjusted until the amplitude of the oscillation of the light passing through the analyzer is substantially constant, and wherein the maximum and minimum intensity of the light passing through the polarizing filter are detected.

4. Apparatus for measuring anisotropy in the reflectivity within a region of a surface, comprising, means for directing a beam of coherent polarized light at the region on the surface, means for directing the reflected light beam through a polarizing filter, means for rotating the polarization directions of both the incident and reflected portions of the beam, and means for detecting the intensity of the light passing through said polarizing filter.

5. Apparatus according to claim 4 including means for adjusting the angle of the surface with respect to the incident and reflected portions of the light beam.

6. Apparatus according to claim 4 wherein said rotating means comprise a rotary half-wave plate.

7. Apparatus according to claim 4 including a universal mount for supporting the surface.

8. A polarizing microscope for measuring optical anisotropy, comprising, a specimen mount, a universal stage, means for directing a beam of coherent polarized light at a specimen in said specimen mount, a polarizing filter positioned to be in the path of the light beam after reflection from the specimen, a rotary half-wave plate positioned to be in the path of the incident and reflected portions of the polarized beam between said specimen mount and said polarizing filter and being oriented such that the incident and reflected portions of the polarized beam traverse through said plate in a direction perpendicular to the plane of said plate, and means for rotating said half-wave plate on an axis which is substantially perpendicular to the plane of said plate.

9. A polarizing microscope according to claim 8 wherein the axes of said universal stage are substantially aligned perpendicular to one another and perpendicular to the axis of the polarizing microscope.

10. A polarizing microscope according to claim 8 wherein said half-wave plate provides a retardance of one-half wave length at a wave length of about 6,328 angstrom units.

11. A polarizing microscope according to claim 8 including means for mounting said polarizing filter for rotation between any two preselected angular positions.

* * * * *

UNITED STATES PATENT AND TRADEMARK OFFICE
CERTIFICATE OF CORRECTION

PATENT NO. : 3,972,619
DATED : August 3, 1976
INVENTOR(S) : Dennis Wakefield Stevens It is certified that error appears in the above-identified patent and that said Letters Patent are hereby corrected as shown below:

Col. 6, line 27 — Delete symbol between "to" and "the".

Claim 3
Col. 7, Line 45 — "in minimum" should be --is minimum--.

Signed and Sealed this

Twenty-fifth Day of January 1977

[SEAL]

Attest:

RUTH C. MASON
Attesting Officer

C. MARSHALL DANN
Commissioner of Patents and Trademarks